US010869736B2

(12) United States Patent
Smith et al.

(10) Patent No.: US 10,869,736 B2
(45) Date of Patent: Dec. 22, 2020

(54) SINGLE X-RAY MARKER

(71) Applicant: XRAYDEPOT LLC, Stafford, VA (US)

(72) Inventors: Van N Smith, Stafford, VA (US);
Kasey Smith, Stafford, VA (US)

(73) Assignee: XRAYDEPOT LLC, Stafford, VA (US)

(*) Notice: Subject to any disclaimer, the term of this patent is extended or adjusted under 35 U.S.C. 154(b) by 0 days.

(21) Appl. No.: 16/020,040

(22) Filed: Jun. 27, 2018

(65) Prior Publication Data

US 2018/0333221 A1 Nov. 22, 2018

Related U.S. Application Data

(63) Continuation-in-part of application No. 29/604,463, filed on May 17, 2017, now Pat. No. Des. 824,520.

(51) Int. Cl.
*A61B 90/00* (2016.01)
*A61B 90/90* (2016.01)
*A61B 90/94* (2016.01)

(52) U.S. Cl.
CPC .............. *A61B 90/39* (2016.02); *A61B 90/90* (2016.02); *A61B 90/94* (2016.02); *A61B 2090/3966* (2016.02)

(58) Field of Classification Search
CPC . A61B 90/39; A61B 90/94; A61B 2090/3966; A61B 90/90
USPC .................................................. 378/162–165
See application file for complete search history.

(56) References Cited

U.S. PATENT DOCUMENTS

| | | | | |
|---|---|---|---|---|
| 4,058,733 A * | 11/1977 | Stembel | ............... | G03B 42/047 378/165 |
| 4,698,836 A * | 10/1987 | Minasian | ............. | G03B 42/047 378/162 |
| 5,345,494 A * | 9/1994 | Willey | ................. | G03B 42/047 378/162 |
| 5,592,527 A * | 1/1997 | Ray | ...................... | G03B 42/047 378/162 |
| 5,640,438 A * | 6/1997 | Talluto | ................. | G03B 42/047 378/162 |
| 6,097,978 A * | 8/2000 | Demarais | .................. | A61F 2/07 378/163 |
| 6,160,870 A * | 12/2000 | Jacobson | ................. | G21K 1/10 378/162 |
| 6,279,579 B1 * | 8/2001 | Riaziat | ................. | A61N 5/1049 128/897 |
| 6,354,737 B1 * | 3/2002 | Hufe | ........................ | H04N 5/32 378/205 |
| 7,092,492 B2 * | 8/2006 | Marn | ..................... | A61B 6/547 378/162 |

(Continued)

*Primary Examiner* — Allen C. Ho

(57) ABSTRACT

A single X-ray marker for use in recording either of two different characters, an "R" or an "L," on an x-ray digital receptor or imaging cassette, corresponding to the "left" or "right" side exposure area of the anatomical part(s) of a patient. The single X-ray marker consists of a base member and several movable parts, which selectively indicate either the "R" or "L" exposure area of the patient. In addition, the single X-ray marker also glows in the dark to facilitate usage in poorly lit areas and includes a radiopaque frame within its base member to help the x-ray technician know that that x-ray technician is not seeing image artifacts.

1 Claim, 5 Drawing Sheets

(56) References Cited

U.S. PATENT DOCUMENTS

| | | | | |
|---|---|---|---|---|
| 7,123,690 | B1* | 10/2006 | Brown | A61B 90/39 |
| | | | | 378/165 |
| 7,575,373 | B2* | 8/2009 | Xu | A61B 6/00 |
| | | | | 378/169 |
| 7,590,221 | B2* | 9/2009 | Durack | A61B 6/4283 |
| | | | | 378/162 |
| 7,602,884 | B1* | 10/2009 | Davis | G01N 33/383 |
| | | | | 378/163 |
| 7,643,615 | B2* | 1/2010 | Wang | G03B 42/02 |
| | | | | 378/162 |
| 7,876,884 | B2* | 1/2011 | Davis | G01N 23/04 |
| | | | | 378/162 |
| 7,978,825 | B2* | 7/2011 | Ngo | G03B 42/047 |
| | | | | 378/163 |
| 8,837,672 | B2* | 9/2014 | Nance | G07D 5/00 |
| | | | | 378/62 |
| 8,903,473 | B2* | 12/2014 | Rogers | A61L 31/18 |
| | | | | 600/395 |
| 8,908,918 | B2* | 12/2014 | Daon | A61B 34/20 |
| | | | | 382/103 |
| 8,923,483 | B2* | 12/2014 | Schneider | A61B 6/467 |
| | | | | 345/641 |
| 9,541,822 | B2* | 1/2017 | Folio | G01C 9/10 |
| D824,520 | S* | 7/2018 | Smith | D24/158 |
| 10,010,372 | B1* | 7/2018 | Beck | A61B 6/505 |

\* cited by examiner

SINGLE X-RAY MARKER

CROSS-REFERENCE TO RELATED APPLICATIONS

This application is a continuation-in-part of U.S. Design Pat. No. D824,520 S issued on 31 Jul. 2018.

BACKGROUND OF THE INVENTION

I. Field of the Invention

The present invention relates generally to medical instruments and more specifically it relates to x-ray imaging identification markers used to identify the left or right side of the anatomical part(s) of a patient, and other indicia taken during x-rays, such as the healthcare facility or the initials of an x-ray technician's name. Particularly, this invention relates to a single identification marker capable of marking either an "R" or an "L" to indicate the anatomical part(s) of a patient that glows in the dark and provides a radiopaque frame around its base to distinguish it from image artifacts on the x-ray image.

Specifically, this invention involves one embodiment of a single x-ray marker capable of indicating either the "R" or "L" side of a patient, and other identification indicia. The invention provides a protective coating on its radiopaque parts to protect the user. The invention also contains glow-in-the-dark features to facilitate use in poorly lit areas.

II. Description of the Related Art

Any discussion of the prior art throughout the specification should in no way be considered as an admission that such prior art is widely known or forms part of common general knowledge in the field.

Medical instruments have been in use for years. Typically, medical instruments vary greatly in configuration depending on what procedure in which the medical instruments are utilized. One such procedure that medical instruments are utilized in are x-ray procedures.

During an x-ray procedure, x-ray markers are generally used to identify the left or right side of the anatomical part(s) of a patient, and other indicia taken during x-rays, such as the healthcare facility or the initials of an x-ray technician's name. The most common identification markers are the two-piece, left and right markers, which may include an x-ray technician's name or initials. These small markers require the technician to keep track of two individual markers, even though only one marker may be required at a given time, and often result in the loss of one or both markers.

Additionally, the markers are frequently in use in dark areas and can be difficult for the technician to find or see during the procedure. Another issue is that image "artifacts" frequently show up on x-ray imaging, such as bullets, jewelry, surgical devices, and other items that are commonly mistaken for the x-ray marker.

In these respects, the x-ray markers according to the present invention substantially depart from the conventional concepts and designs of the prior art, and in doing so provide a single apparatus that is capable of marking either the "R" or "L" side of a patient and other identification indicia, glowing in the dark to facilitate use it low-light areas, and providing a radiopaque frame to eliminate the false identification of image artifacts as the x-ray marker.

BRIEF SUMMARY OF THE INVENTION

In view of the foregoing disadvantages inherent in the known types of medical instruments now present in the prior art, the present invention provides a new x-ray marker that is capable of marking either the "R" or "L" side of a patient and other identification indicia, glowing in the dark to facilitate use in low-light areas, and providing a radiopaque frame to eliminate the false identification of image artifacts as the x-ray marker.

The general purpose of the present invention, which will be described subsequently in greater detail, is to provide a new x-ray marker that has many of the advantages of the medical instruments mentioned heretofore and many novel features that result in a new x-ray marker which is not anticipated, rendered obvious, suggested, or even implied by any of the prior art medical instruments, either alone or in any combination thereof.

To attain this, the present invention generally comprises a base member containing a radiopaque frame and radiopaque parts that can be positioned to form either an "R" or "L" on the base member to indicate the left or right side of a patient in x-ray procedures.

There has thus been outlined, rather broadly, the more important features of the invention in order that the detailed description thereof may be better understood, and in order that the present contribution to the art may be better appreciated. There are additional features of the invention that will be described hereinafter and that will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

A primary object of the present invention is to provide an x-ray marker that will overcome the shortcomings of the prior art devices.

A second object is to provide a single x-ray marker that is capable of indicating either the "R" or "L" side of a patient and other identification indicia.

Another object is to provide an x-ray marker that can be used in poorly lit areas.

An additional object is to provide an x-ray marker that eliminates the possibility of it being mistaken for image artifacts such as bullets, jewelry, surgical devices, and other items that are commonly mistaken for the marker.

A further object is to provide a single x-ray marker to prevent the x-ray technician from carrying two individual markers that are easily lost and misplaced.

Another object is to provide an x-ray marker that is compact, but provides clear and easy to read symbols on the x-ray image.

Another object is to provide an x-ray marker that can be easily cleaned and sanitized.

Another object is to provide a protective coating on the radiopaque material to protect the user during use of the device.

Another object is to provide a marker that can be efficiently and economically produced.

Other objects and advantages of the present invention will become obvious to the reader and it is intended that these objects and advantages are within the scope of the present invention.

To the accomplishment of the above and related objects, this invention may be embodied in the forms illustrated in the accompanying drawings, attention being called to the fact, however, that the drawings are illustrative only, and that changes may be made in the specific construction illustrated and described within the scope of the appended claims.

To accomplish the foregoing and other objects of this invention, there is provided a single identification marker. The device has a primary rectangular base made of radiotransparent and glow-in-the-dark material. The device also contains radiopaque parts capable of forming either an "R" or "L," which designate the left or right side of the anatomical part(s) of a patient being taken during an x-ray procedure. The rectangular base also contains an embedded rectangular piece of radiopaque material that travels along the perimeter of the base to form a frame on the x-ray image around the indicia so that the x-ray technician can be sure that the technician is viewing the indicia on the image and not any image artifacts (such as bullets, surgical devices, jewelry, etc.).

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION OF THE INVENTION

A. Overview

Figure 1:
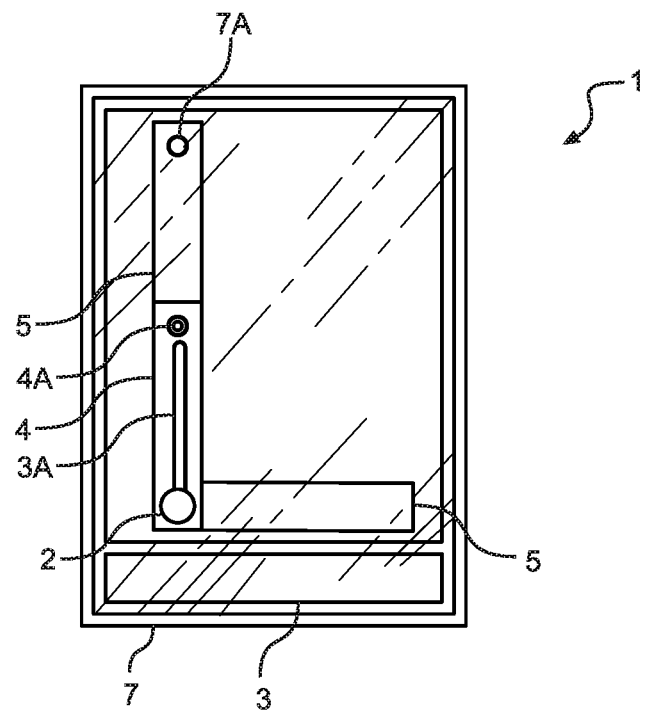
FIG. 1 is a front elevational view of the invention.

Turning now descriptively to the drawings, in which similar reference characters denote simile elements throughout the several views, FIGS. 1 through 9 illustrate one embodiment of a single x-ray marker 1 comprised of parts 2 through 7.

B. Single X-Ray Marker

Figure 4:
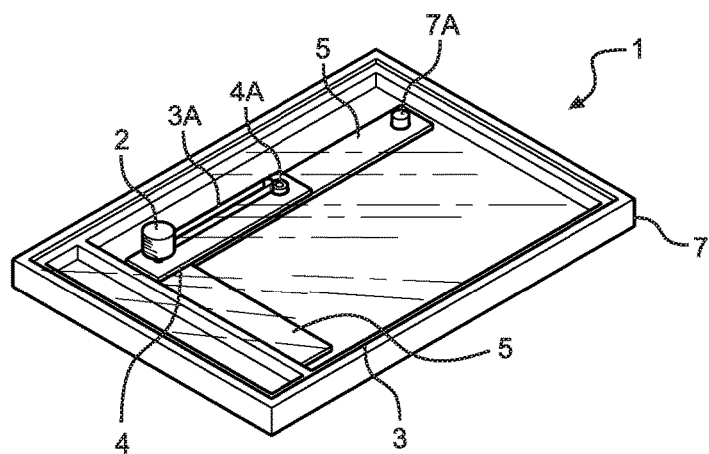
FIG. 4 is a right side perspective view of the invention.

The X-ray marker 1, as shown in FIG. 4, is comprised of a base member 7, slider knob 2, protective window 3, and movable parts 4 though 6. The base member 7 is preferably comprised of a plastic glow-in-the-dark material; however other materials may be utilized in the construction of the base member 7, such as, but not limited to glow-in-the-dark radiotranslucent metal or other glow-in-the-dark radiotranslucent materials. Protective window 3 is preferably comprised of a transparent and radiotranslucent material, such as shatter-resistant glass or plastic.

Figure 3:
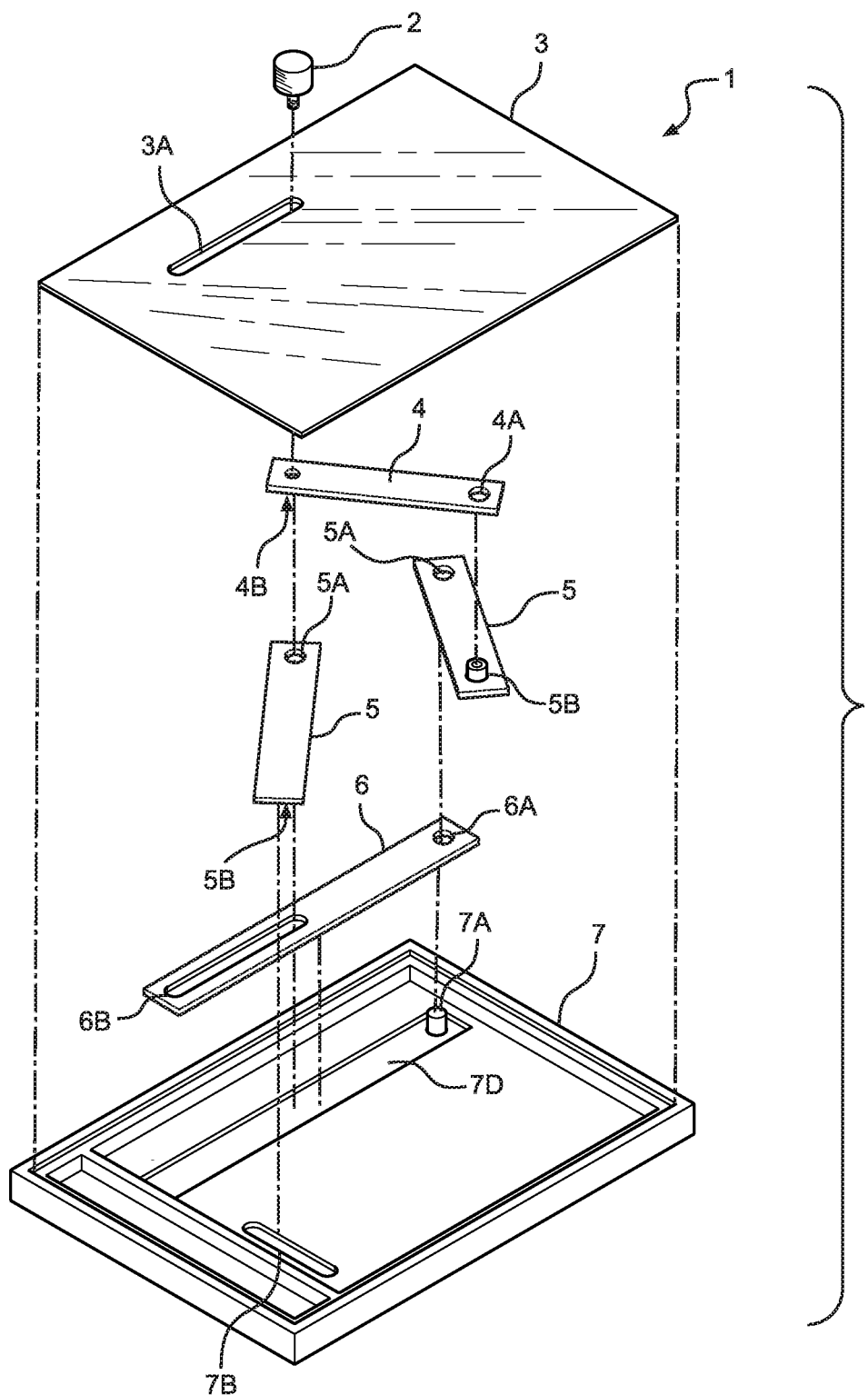
FIG. 3 is an exploded right side perspective view of the invention.
Figure 7:
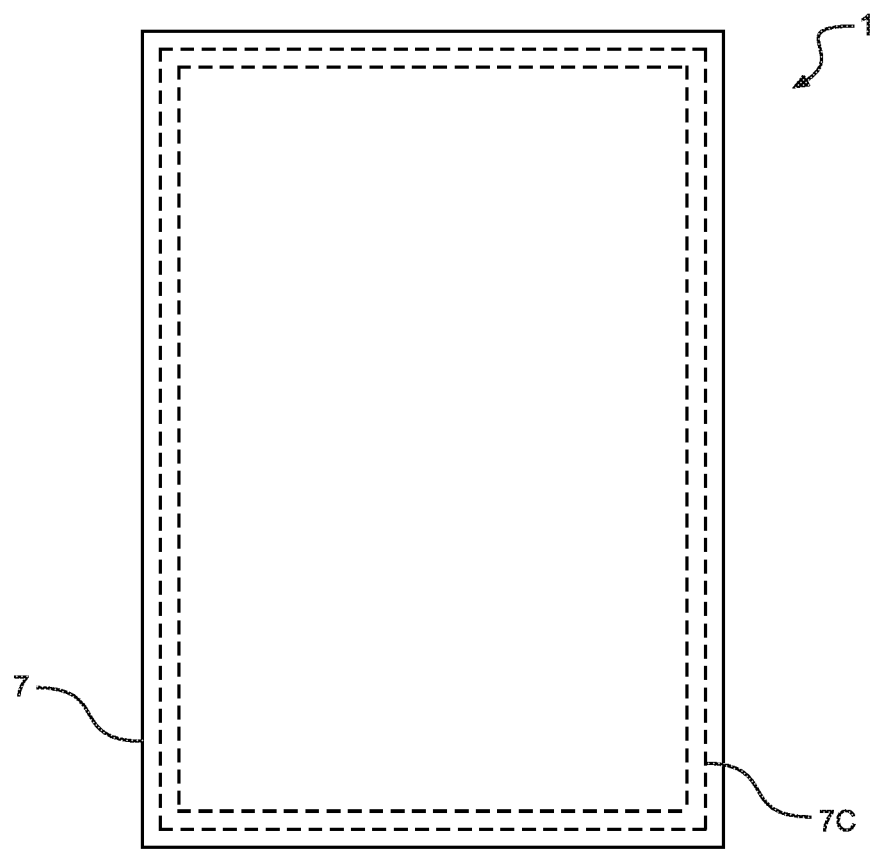
FIG. 7 is a rear elevational view of the invention.

The base member 7 is preferably rectangular in nature and in which is embedded a radiopaque frame 7C comprised of lead or other radiopaque materials, as shown in FIG. 7. The base member 7 contains a vertical, rectangular slot 7D, which contains cylindrical appendage 7A, as shown in FIG. 3, The base member 7 also contains an elliptical horizontal slot 7B, which is located on the lower right hand corner of the base member 7, as shown in FIG. 3. Movable part 6, as shown in FIG. 3, is rectangular in nature and comprised of a radiopaque material such as lead. Movable part 6 has a circular opening 6A at its top end, and vertical elliptical opening 6B at its lower end, as shown in FIG. 3. Movable part 6 fits over base member 7's vertical rectangular slot 7D, with circular opening 6A positioned directly on top of cylindrical appendage 7A, as shown in FIG. 3. The invention contains two movable parts 5 that are rectangular in nature and comprised of a radiopaque material such as lead, and which each contain a circular hole 5A on one end, and cylindrical appendage 5B located on the opposite end, as shown in FIG. 3. The first movable part 5 is flipped over so that its cylindrical appendage 5B fits into elliptical horizontal slot 7B of base member 7, and its circular hole 5A fits over vertical elliptical opening 6B and vertical rectangular slot 7D as shown in FIG. 3. The second movable part 5 is turned upright, so that its circular hole 5A fits over circular opening 6A and base member 7's cylindrical appendage 7A, as shown in FIG. 3. Movable part 4, as shown in FIG. 3, is rectangular in nature and comprised of a radiopaque material such as lead. There is a small cylindrical appendage 4B with a hole drilled all the way through on one end of movable part 4, and a circular opening 4A on the opposite end of movable part 4, as shown in FIG. 3. The small cylindrical appendage 4B of movable part 4 contains a receptacle for the screw at the end of slider knob 2 and fits over the circular hole 5A of the first movable part 5, and the circular opening 4A of movable part 4 fits over the cylindrical appendage 5B of the second movable part 5, as shown in FIG. 3. There is a transparent, protective window 3, which fits over base member 7, as shown in FIG. 3, and is locked into place with glue or other appropriate sealant, and which protects each of movable parts 4 through 6. Protective window 3 is preferably comprised of a transparent and radiotranslucent material, such as shatter-resistant glass or plastic. Protective window 3 contains vertical elliptical opening 3A that fits directly over vertical elliptical opening 6B of movable part 6, as shown in FIG. 3. Slider knob 2 is a cylindrical knob containing a screw at its end, as shown in FIG. 3. Slider knob 2 is comprised of a radiotranslucent material, and is inserted into elliptical vertical opening 3A of transparent protective window 3 and screws into the small cylindrical appendage 4B of movable part 4, facilitating movement of movable parts 4 through 6, and thereby completing the single X-ray marker 1.

Figure 2:
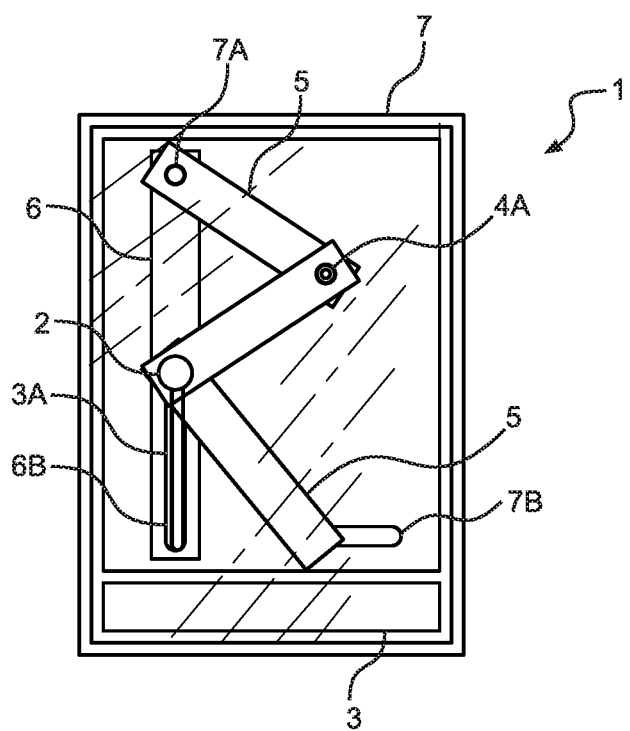
FIG. 2 is a front elevational view of FIG. 1 shown in an alternate position.
Figures 5, 6:
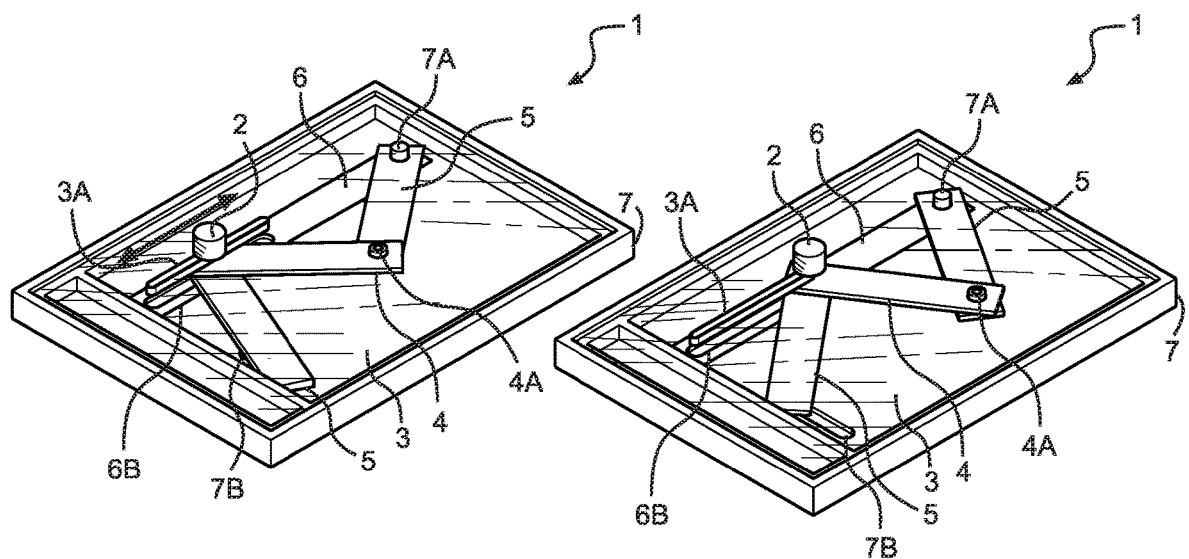
FIG. 5 is a right side perspective view of FIG. 4 shown in an intermediate position.
FIG. 6 is a right side perspective view of FIG. 4 shown in an alternate position.

The fully assembled X-ray marker 1 is then capable of being transformed into an "R" or "L" marker, by moving slider knob 2 along the axes of elliptical vertical opening 3A of protective window 3 and vertical elliptical opening 6B of movable part 6, as shown in FIG. 5. Moving slider knob 2 downward along the axes of vertical elliptical openings 3A and 6B result in the X-ray marker 1 being locked into an "L" position, as shown in FIG. 1. Moving slider knob 2 upward along the axes of vertical elliptical openings 3A and 6B result in the marker being locked into an "R" position, as shown in FIG. 2.

C. In Use

Figure 8:
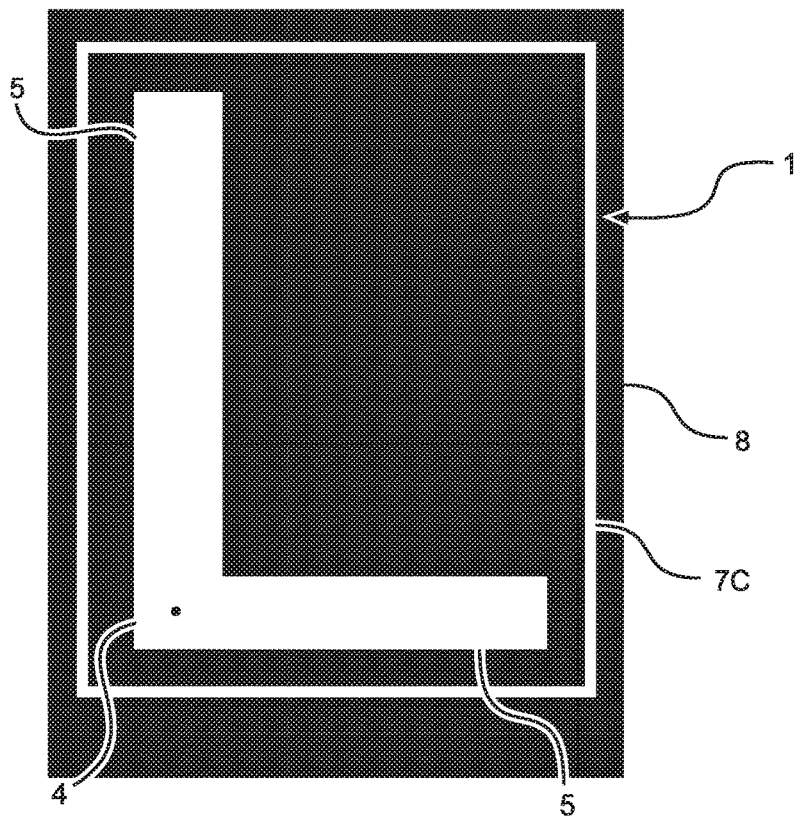
FIG. 8 is a front elevational view of the invention shown in use on x-ray imaging.
Figure 9:
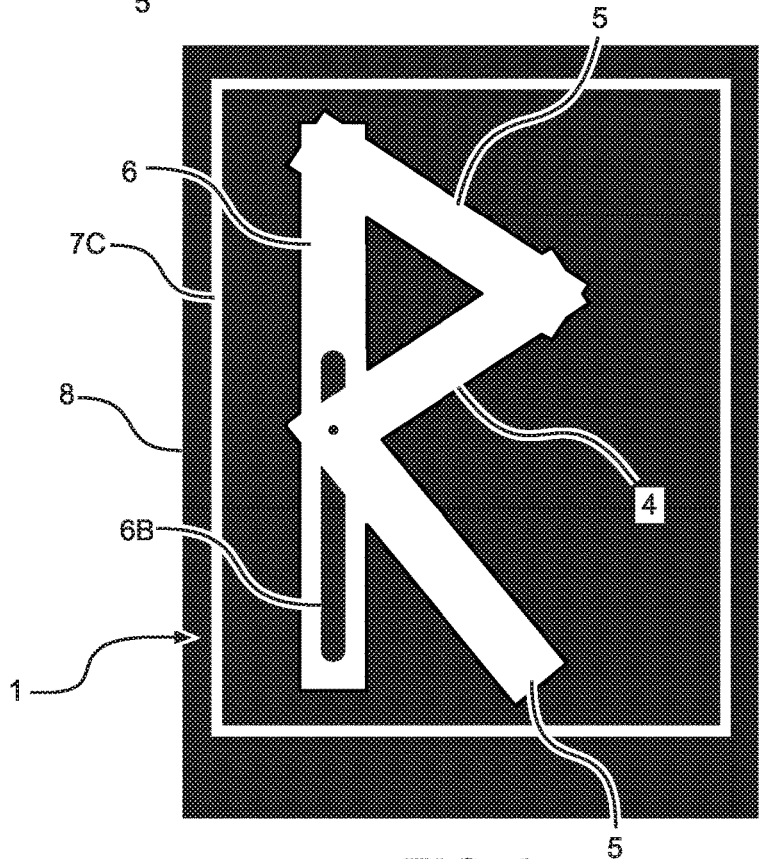
FIG. 9 is a front elevational view of FIG. 8 shown in an alternate position.

In use, the x-ray marker 1 is placed on the imaging cassette or digital receptor 8, as shown in FIGS. 8 and 9. The X-ray marker 1 is preselected into either an "L" marker as shown in FIG. 1 or an "R" marker, as shown in FIG. 2, depending on what side of the patient is being x-rayed. If the left side of the patient is being x-rayed, the "L" comprised of movable part 4 and movable parts 5, and the radiopaque frame 7C will appear on an x-ray image, as shown in FIG. 8. If the right side of the patient is being x-rayed, the "R" comprised of movable part 4, movable parts 5, and movable part 6, and the radiopaque frame 7C will appear on an x-ray image, shown in FIG. 9.

What has been described and illustrated herein is a preferred embodiment of the invention along with some of its variations. The terms, descriptions and figures used herein are set forth by way of illustration only and are not meant as limitations. Those skilled in the art will recognize that many variations are possible within the spirit and scope of the invention, which is intended to be defined by the following claims (and their equivalents) in which all terms are meant in their broadest reasonable sense unless otherwise indicated. Any headings utilized within the description are for convenience only and have no legal or limiting effect.

We claim:
1. A single x-ray marker, comprising:
a base member, a slider knob, a protective window, and several movable parts;
wherein said slider knob controls movement of said several movable parts; and
wherein said slider knob can be moved upwards and downwards along axes of said base member and said protective window to form said several moveable parts into either an "L" position or an "R" position.

* * * * *